United States Patent [19]

Bhongle

[11] Patent Number: 5,639,875

[45] Date of Patent: Jun. 17, 1997

[54] METHODS FOR H-PHOSPHONATE SYNTHEIS OF OLIGONUCLEOTIDES USING TRIPHOSGENE

[75] Inventor: Nandkumar Bhongle, Shrewsbury, Mass.

[73] Assignee: Hybridon, Inc., Worcester, Mass.

[21] Appl. No.: 430,437

[22] Filed: Apr. 28, 1995

Related U.S. Application Data

[63] Continuation-in-part of Ser. No. 382,885, Feb. 2, 1995, abandoned, and Ser. No. 382,250, Feb. 1, 1995, abandoned.

[51] Int. Cl.$^6$ .............................. C07H 1/02; C07H 21/00
[52] U.S. Cl. .......................... 536/25.34; 536/25.3
[58] Field of Search ........................... 536/25.3, 25.34

[56] References Cited

U.S. PATENT DOCUMENTS

| | | | |
|---|---|---|---|
| 5,349,001 | 9/1994 | Greenwald et al. | 525/408 |
| 5,352,803 | 10/1994 | Mattingly | 549/220 |
| 5,405,877 | 4/1995 | Greenwald et al. | 514/772.3 |
| 5,424,414 | 6/1995 | Mattingly | 536/25.32 |

FOREIGN PATENT DOCUMENTS 9202533  2/1992  WIPO.

OTHER PUBLICATIONS

Sakatsume et al. Tetrahedron Lett. 30(46):6375–6378, 1989.
Alexander et al. Collect. Czech. Chem. Commun. 59:1853, 1994.
Alexander et al. Collect. Czech. Chem. Commun. 59:1870, 1989.

*Primary Examiner*—Gary L. Kunz
*Attorney, Agent, or Firm*—McDonnell Boehnen Hulbert & Berghoff

[57] ABSTRACT

New methods of synthesizing mono- and oligo-nucleoside H-phosphonates are disclosed. The methods comprise contacting a mononucleoside with phosphorous acid and triphosgene to yield the corresponding mononucleoside H-phosphonate. A similar procedure can be used to couple a first mononucleoside to a second mononucleoside or to an oligonucleotide, the method comprising contacting, in the presence of triphosgene, a mononucleoside or oligonucleotide having a free 5' hydroxyl with a mononucleoside having a 3' hydroxyl-bearing phosphorous moiety (preferably H-phosphonate).

7 Claims, 2 Drawing Sheets

METHODS FOR H-PHOSPHONATE SYNTHEIS OF OLIGONUCLEOTIDES USING TRIPHOSGENE

This is a continuation-in-part of application U.S. Ser. No. 08/382,885 filed Feb. 2, 1995, now abandoned, and application U.S. Ser. No. 08/382,250, filed Feb. 1, 1995, now abandoned.

BACKGROUND OF THE INVENTION

1. Field of the Invention

This invention relates to new methods of synthesizing mononucleoside H-phosphonates and oligonucleotides using the H-phosphonate method.

2. Summary of the Related Art

There has been much interest in recent years in the use of antisense oligonucleotides as instruments for the selective modulation of gene expression in vitro and in vivo. E.g., Agrawal, *Trends in Biotech.* 10, 152 (1992); Chang and Petit, *Prog. Biophys. Molec. Biol.* 58, 225 (1992). Antisense oligonucleotides are constructed to be sufficiently complementary to a target nucleic acid to hybridize with the target under the conditions of interest and inhibit expression of the target. Antisense oligonucleotides may be designed to bind directly to DNA (the so-called "anti-gene" approach) or to mRNA. Id. Expression inhibition is believed to occur by prevention of transcription or translation, or inducement of target mRNA cleavage by RNase H.

Antisense oligonucleotides can be used as a research tool in vitro to determine the biological function of genes and proteins. They provide an easily used alternative to the laborious method of gene mutation (e.g., deletion mutation) to selectively inhibit gene expression. The importance of this method is readily appreciated when one realizes that the elucidation of all known biological processes was determined by deletion mutation.

Antisense oligonucleotides also may be used to treat a variety of pathogenic diseases by inhibiting nucleic acid expression of the pathogen in vivo.

Simple methods for synthesizing and purifying oligonucleotides are now in great demand due to the utility of synthetic oligonucleotides in a wide variety of molecular biological techniques. Initially, the method of choice for synthesizing oligonucleotides was the beta-cyanoethyl phosphoramidite method. Beaucage and Caruthers, *Tetrahedron Lett.* 22, 1859 (1981). In the phosphoramidite procedure, the first nucleotide (monomer 1) is bound by its 3'-hydroxyl to a solid matrix while its 5'-hydroxyl remains available for binding. The synthesis of the first internucleotide link is carried out by mixing bound monomer 1 with a second nucleotide that has a reactive 3'-diisopropyl phosphoramidite group on its 3'-hydroxyl and a blocking group on its 5'-hydroxyl (monomer 2). In the presence of a weak acid, coupling of monomer 1 and monomer 2 occurs as a phosphodiester with the phosphorus in a trivalent state. This is oxidized, giving a pentavalent phosphotriester. The protecting group is then removed from monomer 2 and the process is repeated.

The H-phosphonate approach was first reported by Hale et al., *J. Chem. Soc.*, 3291 (1957) and revisited some twenty years later by Sekine and Hata, *Tetrahedron Lett.* 16, 1711 (1975), Sekine et al., *Tetrahedron Lett.* 20, 1145 (1979), Garegg et al., *Chemica Scripta* 25, 280 (1985) ("Garegg I"), and Garegg et al., *Chemica Scripta* 26, 59 (1986) ("Garegg II"). The H-phosphonate method involves condensing the 5' hydroxyl group of the nascent oligonucleotide with a nucleoside having a 3' phosphonate moiety. Once the entire chain is constructed, the phosphite diester linkages are oxidized with t-butyl hydroperoxide or iodine to yield the corresponding phosphotriester. See, e.g., Froehler, "Oligodeoxynucleotide Synthesis," in *Methods in Molecular Biology*, Vol. 20, *Protocols for Oligonucleotides and Analogs*, p. 63–80 (S. Agrawal, Ed., Humana Press 1993) ("Froehler I"); Uhlmann and Peyman, *Chem. Rev.* 90, 543 (1990).

The H-phosphonate approach became practical only with the introduction of pivaloyl chloride as the condensing agent. Sterically hindered carbonyl chlorides such as adamantoyl and pivaloyl chloride (trimethyl acetyl chloride) are typically used as condensing agents. U.S. Pat. No. 4,959, 463; European Pat. App. 86307926.5. Since then there have been reports of successful use of this method in both deoxyribonucleotide (Garegg et al., *Tetrahedron Lett.*, 27, 4051 (1986) ("Garegg III"); Froehler et al., *Nucl. Acid. Res.* 14, 5399 (1986) ("Froehler II")) and ribonucleotide syntheses (Garegg et al., *Tetrahedron Lett.* 27, 4055 (1986) ("Garegg IV")). See generally Stawinski, "Some Aspects of H-Phosphonate Chemistry," in *Handbook of Organophosphorus Chemistry*, pp. 377–434 (R. Engel, Ed., Marcel Dekker, Inc., New York 1992). The H-phosphonate method offers several advantages over the beta-cyanoethyl phosphoramidite method. The 3'-phosphonate monomers are easily prepared and are stable to hydrolysis and oxidation. H-phosphonate chemistry requires no phosphate protecting group because phosphite diester linkages are relatively inert to coupling conditions. Furthermore, the H-phosphonate method requires a shorter cycle time. Finally, a simple reaction can be used to prepare backbone-modified DNA and RNA from the H-phosphonate synthesis product.

The H-phosphonate methods of Froehler I, Garegg III, and Garegg IV, supra, although adequate for small scale synthesis (i.e., less than 1 μmol), are not practical on a large scale (e.g., 10–20 μmol). The main reason is that the methods reported by these groups require 20–30 equivalents of monomer per coupling reaction. At this rate, the monomer consumption costs represent approximately 60% of the oligonucleotide assembly cost.

Gaffney et al., *Tetrahedron Lett.* 29, 2619 (1988), reported an effort to scale up H-phosphonate oligonucleotide synthesis to the 10–20 μmol range while reducing the monomer equivalents consumed per coupling reaction. In synthesizing an 8-mer (consuming 1.53 equivalents of H-phosphonate) and a 26-mer (consuming 5.5 equivalents of H-phosphonate), however, Gaffney's group reported an average coupling yield of only 81% and 87%, respectively. Because of this relatively low coupling efficiency as compared with prior art methods, the authors found it necessary to employ a separate capping step using cyanoethyl H-phosphonate to prevent the elongation of truncated failed sequences in subsequent synthetic cycles. This extra step was necessary because the self-capping efficiency for pivaloyl chloride was found to be too low. According to the method of Gaffney et al., which assumed a 94% coupling yield, the expected result of a 20-mer synthetic reaction would be a crude mixture consisting of 24% product (20-mer) and 76% short chains (e.g., 19-mers, 18-mers, etc.).

Decreased yields are due in large part to some side reactions between the condensing agent and starting material. Efimov et al., *Nucl. Acids Res.* 21, 5337 (1993), demonstrated the use of dipentafluorophenyl carbonate as an activating agent for the H-phosphonate reaction. Use of this compound resulted in a high coupling efficiency with a concomitant decrease in side reactions.

A variety of methods of preparing mononucleoside H-phosphonates have been proposed, including PCl$_3$/azole system (Garegg II, supra; Froehler II, supra), salicylchlorophosphite (Marugg et al., *Tetrahedron Lett.* 27, 2661 (1986) ), di- and tri(2,2,2-trifluoroethyl) H-phosphonates (Gibbs and Larsen, *Synthesis-Stuttgart*, pp. 410–413 (1984), pyro-H-phosphonate (Sakatsume et al., *Nucleic Acids Res.* 17, 3689 (1989), and transesterification of diphenyl H-phosphonate (Jankowska et al., *Tetrahedron Lett.* 35, 3355 (1994).

Other methods include oxidative phosphitylation of nucleosides with phosphinic acid in the presence arene sulfonyl derivatives using suitably protected nucleosides. Sekine and Hata, supra. Sekine et al., *Tetrahedron Lett.* 29, 1037 (1988), used phosphonic acid with mesitylenedisulfonyl chloride, but observed a significant side reaction comprising formation of bisnucleoside H-phosphonate diesters. The result was oxidation of the desired H-phosphonate monoesters by the condensing reagent. Garegg et al., *J. Chem. Soc. Perkin Trans. II.*, pp. 1209–1214 (1987). Replacement of sulfonyl chloride with pivaloyl chloride did not reduce this side reaction.

Stawinski and Thelin, *Nucleosides & Nucleotides* 9, 129 (1990), found that they could produce the H-phosphonate monoesters almost exclusively if the phosphonic acid is first converted to pyrophosphonate, which can be done in the presence of the nucleoside and condensing reagent.

While there has been much interest and work on the development of methods for fast and efficient oligonucleotide synthesis, improved methods are still desirable.

SUMMARY OF THE INVENTION

Disclosed herein is an improved method of synthesizing oligonucleotides by the H-phosphonate approach. In one aspect of the invention, a new method of synthesizing mononucleoside H-phosphonates is disclosed. This method comprises contacting a 5'- and base-protected mononucleoside with phosphorous acid and triphosgene at room temperature. The resulting product is the desired mononucleoside H-phosphonate.

In a second aspect of the invention, a new method of coupling nucleosides is presented. The method comprises contacting a 5'-protected nucleoside or oligonucleoside having a 3'-phosphonate moiety with a 3'-protected mononucleoside have a free 5'-hydroxyl in the presence of triphosgene.

In a third aspect of the invention, a new method of synthesizing oligonucleotide phosphodiesters and phosphorothioates is presented. The method comprises repeated nucleoside coupling according to the second aspect of the invention followed by oxidation to produce the phosphodiester or oxidative sulfurization to produce the phosphorothioate.

These methods advantageously use triphosgene, which is a safe, stable, and commercially available crystalline solid. Triphosgene is easy to handle and less hygroscopic than other acid chlorides typically used in H-phosphonate chemistry. These properties make triphosgene attractive for large scale synthesis of oligonucleotides.

The foregoing merely summarizes certain aspects of the present invention and is not intended, nor should it be construed, to limit the invention in any way. All of the patents and other publications recited in this specification are hereby incorporated by reference in their entirety.

DETAILED DESCRIPTION OF THE PREFERRED EMBODIMENTS

The present invention generally comprises new methods for synthesizing nucleoside monomers useful for constructing oligonucleotides by the H-phosphonate method as well as methods for constructing nucleoside multi- and oligomers.

Figure 1:
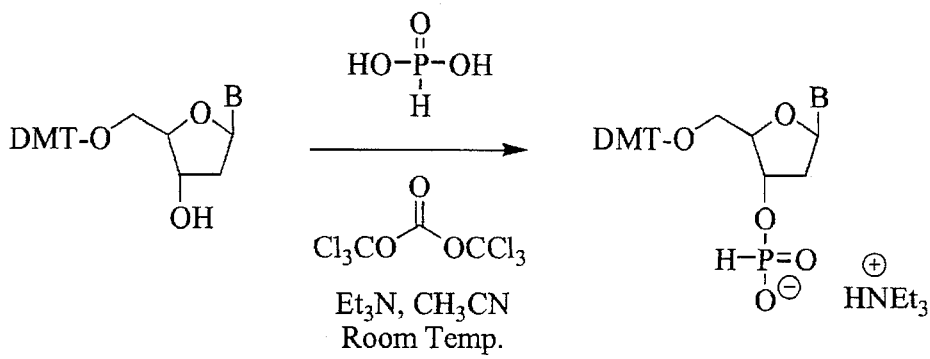
FIG. 1 displays the addition of an H-phosphonate moiety to a mononucleoside and the efficiencies of the addition to several mononucleosides.

In a first aspect of the invention, a new method is provided for the synthesis of nucleoside H-phosphonate monomers. The method comprises contacting a mononucleoside having a 3'-hydroxyl moiety with triphosgene and an excess of phosphorous acid ($H_3PO_3$). FIG. 1. $^{31}$P NMR revealed that the phosphorous acid and triphosgene first produce a pyrophosphonate intermediate. The intermediate then reacts with the mononucleoside 3'-hydroxyl to yield the desired mononucleoside H-phosphonate product. Preferably, the mononucleoside is suitably protected, for example, at the 5'-position (e.g., with DMT) and, if necessary, at the base.

The reaction is exothermic and proceeds at room temperature in any suitable solvent. In a preferred embodiment, the solvent is a 1:1 mixture of acetonitrile and triethylamine. Because the reaction is exothermic, when used in large scale the temperature should be monitored carefully for rapid and excessive heating and cooled if necessary.

As used herein, the terms "suitable" and "suitably," when used to describe a general class of compounds, methods, or techniques (as the case may be) that serves a desired function means any compound, method, or technique of that class that does not cause or induce undesirable side effects that would either defeat the purpose for which the compound, method, or technique is used, or, on balance, outweigh the benefits of using the particular compound, method, or technique. For example, as used herein, a "suitable solvent" is any solvent that is capable of dissolving the starting materials, permits the reaction to proceed, and does not itself chemically react with the starting or ending materials. A suitable protecting group is one that prevents reaction at the site to which it is bound and that can be cleaved without altering the molecule that it protects.

For convenience, as used herein the term oligonucleotide refers to any nucleic acid chain comprising two or more nucleosides.

Figure 2:
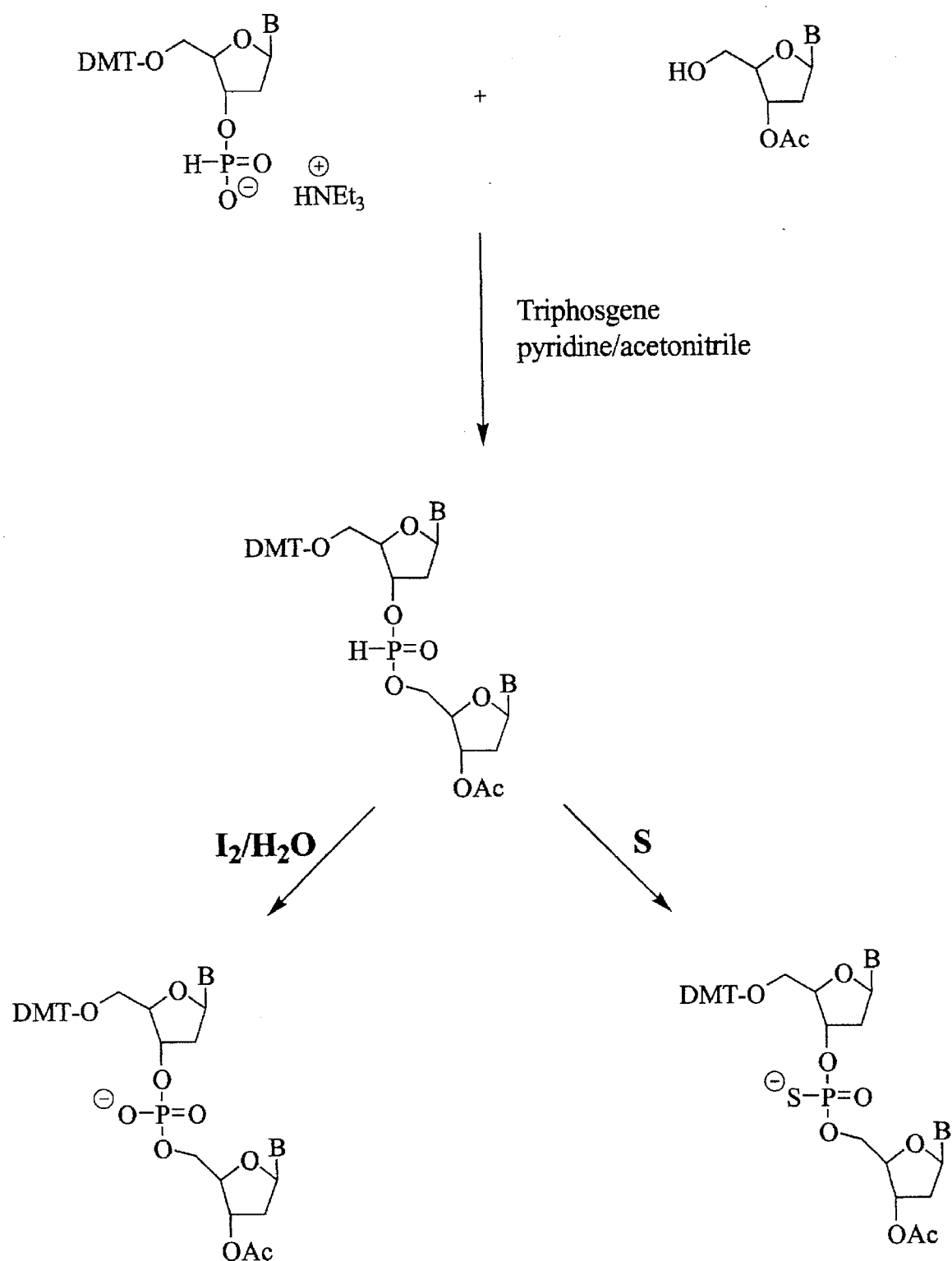
FIG. 2 displays the coupling of two mononucleosides by the method of the invention.

In a second aspect of the present invention, a new method is provided for the synthesis of dinucleosides. This method comprises contacting, in the presence of triphosgene, a first mononucleoside having a hydroxyl-bearing phosphorous moiety at the 3'-position (preferably H-phosphonate) with a second mononucleoside having a free 5'-hydroxyl. The result is a dinucleoside H-phosphonate. FIG. 2. Preferably, the first mononucleoside is suitably protected, for example, at the 5'-O position (e.g., by DMT) and, if necessary, at the base, and the second mononucleoside is suitably protected at the 3'-O (e.g., by an acetyl moiety) and, if necessary, the base. Any suitable solvent may be used. In a preferred embodiment, the solvent is pyridine.

In a third aspect of the present invention, a new method is provided for the synthesis of oligonucleotides. This method comprises contacting, in the presence of triphosgene, a nascent oligonucleotide having a free 5'-hydroxyl moiety with a mono- or oligo- nucleotide having a 3'-hydroxyl-bearing phosphorous moiety (preferably H-phosphonate) to yield an oligonucleotide H-phosphonate that is one or more nucleotide(s) greater in length (depending on whether a mono- or oligo-nucleotide was used). The resulting oligonucleotide can then be treated with additional nucleosides (mono- or oligo-) in the presence of triphosgene to further increase its length. This procedure is repeated until the desired oligonucleotide sequence has been synthesized. The nascent oligonucleotide can be of any conveniently synthesized length and is preferably anchored to a solid support. Preferably, the oligonucleotide is suitably protected, for example, at its 3' end (e.g., by the solid support) and, if necessary, at the bases, and the mono- or oligo-nucleotide is suitably protected at the 5'-O end (e.g., by DMT) and, if necessary the base or bases.

In a preferred embodiment of the third aspect of the invention, a solid support is loaded with mononucleoside. Many such methods are known to those skilled in the art. E.g., Pon, "Preparation of Solid Phase Supports," in *Methods in Molecular Biology*, vol. 20, pp. 465–496 (S. Agrawal, Ed., Humana Press, Totawa N.J. 1993) and references cited therein. The desired oligonucleotide is incrementally synthesized by the foregoing method by the addition of mononucleosides or di- or tri-nucleoside building blocks. Preferably, the desired oligonucleotide is synthesized in increments of one nucleoside at a time.

Oligonucleotides synthesized according to either the second or third aspects of the invention may be subjected to oxidation with, for example, iodine to yield an oligonucleotide in which the H-phosphonate internucleoside linkages are converted to phosphodiesters. Froehler, id. at 63–80. Alternatively, the oligonucleotide H-phosphonate may be subjected to oxidative sulfurization (e.g., Iyer et at., *J. Org. Chem.* 55, 4693 (1990)) to yield an oligonucleotide in which the H-phosphonate internucleoside linkages have been converted to phosphorothioates.

The methods according to the invention are advantageously used with either ribo- or deoxyribo-mononucleosides and oligonucleotides. Ribonucleotides will have to be protected at the 2'-O position.

The following examples are offered for illustrative purposes only and are not intended, nor should they be construed, to limit the invention in any way.

EXAMPLES

Example 1
Synthesis of DMT-protected thymidine H-phosphonate

Triphosgene (0.907 g, 3.06 mmol) (Aldrich, Milwaukee, Wis.) was added in small lots to a stirring solution of phosphorous acid (0.753 g, 9.18 mmol) (Aldrich, Milwaukee, Wis.) and dimethoxytrityl thymidine (0.5 g, 0.91 mmol) (Chem Empex Int'l, Wooddale, Ill.) in 16 ml of acetonitrile (Burdick Jackson, Muskegon, Mich.)/ triethylamine (Aldrich, Milwaukee, Wis.) (1:1). The reaction was exothermic, warming to about 40° C. during the reaction. The reaction mixture was stirred at room temperature for two hours. TLC at this point indicated the presence of both the starting material and the product. An additional amount of triethylamine (5 ml) and triphosgene (0.455 g, 1.53 mmol) were added successively and the reaction was stirred at room temperature for an additional two hours. TLC showed complete disappearance of the starting material. The reaction was quenched with 10 ml of 0.5N triethylammonium bicarbonate (made by reacting triethyl amine with dry ice in aqueous medium) and the volatiles were evaporated off. The aqueous layer was extracted with methylene chloride (3×20 ml) (EM Science, Gibbstown, N.J.) and dried over sodium sulfate (Em Science, Gibbstown, N.J.), evaporating methylene chloride to give a pale yellow solid (0.584 g, yield=89.7%). The crude product was found to be of good purity. It was characterized by $^1$H and $^{31}$P NMR.

The results of the foregoing synthesis conducted on several nucleosides is presented in FIG. 1 and Table 1. For each of the experiments presented in Table 1, an initial amount of reactants (recited in the upper row of each experiment in Table 1) were mixed and reacted at room temperature for 2 hours. Subsequently, an additional amount of triethylamine followed by an additional amount of triphosgene (recited in the lower row of each experiment in Table 1) were added to the mixture and the reaction allowed to proceed an additional two hours at room temperature before the product was isolated. The ribonucleotides were methylated at the 2'-O position.

TABLE 1

| Nucleoside (g, mmol) | Phosphorous acid (g, mmol) | Triphosgene (g, mmol) | Et$_3$N (ml) | CH$_3$CN (ml) | Crude Yield (g, %) |
|---|---|---|---|---|---|
| DMT-T | 0.753, 9.18 | 0.907, 3.06 | 8 | 8 | |
| 0.5, .091 | | 0.455, 1.53 | 5 | | 0.584, 89.7 |
| DMT-N-Bz-dC | 0.647, 7.90 | 0.780, 2.62 | 10 | 10 | |
| 0.5, 0.79 | | 0.390, 1.31 | 5 | | 0.423, 67.1 |
| DMT-N-Bz-dA | 0.623, 7.60 | 0.751, 2.53 | 8 | 8 | |
| 0.5, 0.76 | | 0.375, 1.26 | 4 | | 0.573, 91.7 |
| DMT-N-iBu-dG | 0.640, 7.80 | 0.773, 2.60 | 8 | 8 | |
| 0.5, 0.78 | | 0.386, 1.3 | 5 | | 0.403, 64.0 |
| DMT-U | 0.146, 1.80 | 0.176, 0.59 | 1.5 | 1.5 | |
| 0.1, 0.18 | | 0.100, 0.34 | 1.5 | | 0.104, 80.6 |
| DMT-N-Bz-rA | 0.119, 1.50 | 0.143, 0.48 | 1.5 | 1.5 | |
| 0.1, 0.15 | | 0.100, 0.34 | | | 0.087, 70.2 |

Example 2

Synthesis of a Nucleotide Dimer using the Triphosgene Method

Triphosgene (0.020 g) was added at room temperature to a solution of DMT-thymidine H-phosphonate, triethylammonium salt (0.100 g) (Sigma Chemical, St. Louis, Mo.) and 3'O-acetylthymidine (0.040 g) in 2 ml of pyridine (Burdick Jackson, Muskegon, Mich.). TLC analysis after 2 hours showed the presence of the starting materials along with that of the products. An additional amount of triphosgene (0.020 g) was added and the reaction was stirred at room temperature for 3 hours. TLC analysis revealed complete disappearance of the starting materials. The reaction mixture was poured into 10 ml of water and extracted with methylene chloride (3×10 ml). The methylene chloride layer was dried over sodium sulfate and evaporated to give 0.165 g of brown solid. The brown solid was dissolved in 2 ml of pyridine, 0.100 g of elemental sulfur (J. T. Baker, Phillipsburg, N.J.) was added, and the reaction stirred at room temperature overnight. 2 ml of triethylamine was added and the reaction was continued for 30 minutes. The reaction was poured into 10 ml of water and extracted with methylene chloride (3×10 ml). The methylene chloride layer was dried over sodium sulfate (EM Science)and methylene chloride evaporated to give 0.150 g of a brown solid, the T-T dimer.

I claim:

1. A method of synthesizing a mononucleoside H-phosphonate comprising contacting a mononucleoside having a free 3'-hydroxyl moiety with phosphorous acid and triphosgene.

2. A method of synthesizing a dinucleoside comprising contacting, in the presence of triphosgene, a mononucleoside having H-phosphonate at the 3'-position with a mononucleoside having a free 5'-hydroxyl group.

3. A method of coupling a first mono- or oligo-nucleoside to a second mono- or oligo-nucleoside comprising contacting, in the presence of triphosgene, a first mono- or oligo-nucleoside having H-phosphonate at the 3'-position with a second mono- or oligo-nucleoside having a free 5'-hydroxyl group.

4. The method of claim 3 wherein the first and second nucleosides are mononucleosides.

5. The method or claim 3 wherein the first nucleoside is a mononucleoside and the second nucleoside is a support-bound oligonucleotide.

6. A method of synthesizing an oligonucleotide comprising:

(a) loading a solid support with a 5'-protected mononucleoside;

(b) cleaving the 5'-protecting group;

(c) contacting, in the presence of triphosgene, the mononucleoside with a 5'-protected mono- or oligo-nucleoside having a 3'-H-phosphonate to produce a 5'-protected nascent oligonucleotide;

(d) cleaving the nascent oligonucleotide's 5'-protecting group;

(e) contacting, in the presence of triphosgene, the nascent oligonucleotide of (d) with a 5'-protected mono- or oligo-nucleoside having a 3'-H-phosphonate to produce a nascent oligonucleotide having one or more additional nucleosides;

(f) repeating (d) and (e) sequentially until an oligonucleotide of the desired sequence is obtained;

(g) oxidizing the oligonucleotide of (f) to yield a phosphodiester or phosphorothioate.

7. The method according to claim 6 wherein the nascent oligonucleotide is incrementally increased in length by one nucleoside at a time.

* * * * *